United States Patent [19]

Mower

[11] Patent Number: 4,559,946
[45] Date of Patent: Dec. 24, 1985

[54] METHOD AND APPARATUS FOR CORRECTING ABNORMAL CARDIAC ACTIVITY BY LOW ENERGY SHOCKS

[75] Inventor: Morton M. Mower, Lutherville, Md.

[73] Assignee: Mieczyslaw Mirowski, Owings Mills, Md.

[21] Appl. No.: 389,907

[22] Filed: Jun. 18, 1982

[51] Int. Cl.[4] ............................................. A61N 1/36
[52] U.S. Cl. ........................ 128/419 D; 128/419 PG
[58] Field of Search ......... 128/419 P, 419 PG, 419 D

[56] References Cited

U.S. PATENT DOCUMENTS

| Re. 27,652 | 5/1973 | Mirowski et al. | |
|---|---|---|---|
| 3,942,536 | 3/1976 | Mirowski et al. | |
| 4,184,493 | 1/1980 | Langer et al. | |
| 4,270,549 | 6/1981 | Heilman | |
| 4,384,585 | 5/1983 | Zipes | 128/419 PG |
| 4,393,877 | 7/1983 | Imran | 128/419 D |

FOREIGN PATENT DOCUMENTS 0023134  1/1981  European Pat. Off. .

Primary Examiner—Kyle L. Howell
Assistant Examiner—Francis J. Jaworski
Attorney, Agent, or Firm—Fleit, Jacobson, Cohn & Price

[57] ABSTRACT

The present invention relates to a method and apparatus for delivering two or more individual low-level pulses to correct certain cardiac arrhythmias such as high-rate ventricular tachycardia and ventricular fibrillation; at least the latter shocks are delivered in synchronism with a repeatable characteristic of the heart's electrical activity. Basically, the apparatus comprises an electrode sensor placed in the right ventricle of the heart or in the coronary sinus to act as a detector for the electrical activity of the heart. Connected to the electrode sensor is an arrhythmia detector chosen to detect such arrhythmias as ventricular tachycardia and ventricular fibrillation. Upon detection of one of these arrhythmias, the detector issues a signal which is interpreted by a programmable logic device to activate an energy storage device for delivering a first low-level shock to the heart through a shock delivering electrode. A slew rate detector is then activated by the logic device. The output of the slew rate detector is fed to a comparator to be compared with a continually updated reference signal supplied by the logic device. When the slew rate output equals or exceeds the value of the reference signal, the comparator issues a signal which activates the energy storage device to issue a second low-level shock to the heart through the shock delivering electrode. Additional shocks may be delivered in a manner similar to the delivery of the second shock under the control of the logic device.

13 Claims, 3 Drawing Figures

METHOD AND APPARATUS FOR CORRECTING ABNORMAL CARDIAC ACTIVITY BY LOW ENERGY SHOCKS

BACKGROUND OF THE INVENTION

1. Field of the Invention

The present invention relates to a method and apparatus for correcting abnormal cardiac activity by employing low energy shocks. More specifically, the present invention deals with the correction of arrhythmias such as high-rate ventricular tachycardia and ventricular fibrillation with multiple relatively low energy shocks issued in synchronism with a repeatable event in the arrhythmia.

2. Description of the Prior Art

Normal heart rhythm (sometimes called "sinus rhythm") originates in the sino-atrial (SA) node of the heart. Disorders of heart rhythm are called arrhythmias, and may arise in either the atria or the ventricles. For example, one type of arrhythmia manifests itself in the form of a rapid heart rate (known as "tachycardia") arising in the atria, which may be serious in patients with diseased hearts.

A common treatment for serious tachycardia consists, basically, in passing a pulse of electrical energy through the heart, and momentarily stopping the heart completely, after which the heart is left to start spontaneously in sinus rhythm. The instrument utilized for such treatment is known as a cardioverter. This instrument is in most respects the same as the instrument known as the defibrillator, with the major difference being that the cardioverter typically delivers its shocks in synchrony with the cardiac activity so as to avoid the vulnerable period and hence lessen the possibility of worsening the rhythm being treated. Specifically, the delivery of electrical energy in the vulnerable period (e.g., on the T-wave) could induce ventricular fibrillation.

Additionally, cardioverting pulses often are characterized by energy levels of approximately 25 to 100 joules externally, whereas the energy levels typically employed for ventricular defibrillation are in the range of 100-400 joules for external application (or 20-50 joules for internal application). For purposes of comparison, pacing is accomplished by energy levels on the order of 0.04 millijoules or less.

Ventricular fibrillation is an arrhythmia generally more difficult to break than tachycardia. As noted previously, the energies required to defibrillate generally are higher than those capable of cardioverting. And, there are several phenomena involved in ventricular defibrillation that are not adequately explained by the conventional theory that a defibrillating shock needs to be sufficiently strong to depolarize the vast majority (a critical mass) of the myocardium. For example, it has been observed that a heart not defibrillated by several shocks at a particular energy level suddenly responds to the same energy level and reverts to sinus rhythm. It further has been observed that at times a heart may not respond to high energy shocks, but effectively can be defibrillated if the energy is reduced to a lower level.

There are obvious reasons for wanting to defibrillate at low energy levels, and hence there have been efforts made to reduce the energy levels in defibrillation. Some low energy defibrillation techniques have been described, but although at times effective, such techniques are not consistently so. For example, a double pulse low energy system is described by Jan Kugelberg in the article "Ventricular Defibrillation—A New Aspect" (Stockholm, Sweden: Acta Chirurgica Scandinavica, 1967). Kugelberg discloses the use of two pulses separated by a predetermined time period, optimally 100 miliseconds. The theory is that the first pulse affects and synchronizes a small portion of the myocardium, while the second pulse then can more easily complete the job of reverting the arrhythmia. While the theory does appear to have some merit, and while experimentation has shown approximately 60% effectiveness with laboratory dogs at the optimal pulse interval of 100 milliseconds, the Kugelberg technique has not been accepted as a viable approach to defibrillation at low energies.

Another low-energy theory previously advanced involves what is termed the "protective zone" theory. This theory is that a properly timed small shock can prevent desynchronization of myocardial depolarization which otherwise could lead to ventricular fibrillation when shocks are delivered in the vulnerable period. A timed second shock, according to this theory, resynchronizes the myocardial fibers which were disrupted by the first shock. But, again, this theory has not consistently been effective in practice.

Defibrillation of the heart also has been effected by relatively low energy shocks delivered through an intravascular catheter. In this regard, it has been observed that catheter defibrillation in man often is effective using 5-15 watt seconds. See commonly owned Mirowski et al U.S. Pat. No. 3,942,536, incorporated by reference herein. Still, there is benefit to be gained by further reducing energy levels.

It is believed that the inability to obtain consistently favorable results at low energy levels with the prior art methods can be linked to the inherent random delivery of shocks in response to the malignant arrhythmias. There is thus a need for a method and apparatus which is effective in uniformly correcting certain cardiac arrhythmias with shocks having energy levels lower than those presently employed with the techniques of the prior art. The present invention is directed toward filling such need.

SUMMARY OF THE INVENTION

The present invention relates to a method and apparatus for delivering two or more individual low-level pulses, at least the latter of which are delivered in synchronism with a repeatable characteristic of the arrhythmia being treated, to correct certain cardiac arrhythmias such as high-rate ventricular tachycardia and even ventricular fibrillation.

Basically, the apparatus comprises a sensitive detector of the heart's electrical activity, a pair of discharge electrodes, circuitry for recognizing treatable arrhythmias, and timing circuitry for effecting plural discharges in synchronism with a repeatable characteristic of the heart's electrical activity.

In one embodiment, the detector is in the form of a high resolution ECG bipolar electrode sensor having two spaced electrodes; the electrode sensor is designed to reside in the right ventricle. The discharge, or shock delivering electrode, may be in the form of a bipolar catheter having two separated electrodes adapted to be placed, respectively, in the right ventricle and in the superior vena cava. Alternatively, the discharge electrodes can take the form of a unipolar catheter in the superior vena cava (which could reside on the sensor catheter) and a single patch electrode placed over the apex of the heart. It also is contemplated to use two epicardial patch electrodes positioned, respectively, at the apex and the base of the heart. Further, the same electrodes can serve both for delivering the low-level shocks and for monitoring ECG activity.

Connected to the electrode sensor is an arrhythmia detector chosen to detect, for example, such arrhythmias as ventricular fibrillation, ostensibly a very disorganized cardiac rhythm, and ventricular tachycardia, a somewhat more organized cardiac rhythm by comparison. Upon detection of one of these arrhythmias, the detector issues a signal which is interpreted by a programmable logic device to activate an energy storage device for delivering a first low-level shock to the heart through the bipolar catheter, the epicardial electrodes, or a combination of the two. As used herein, a low-level shock is one within the range of 0.1-15 joules.

A slew rate detector, which is operatively connected to the sensing electrodes, is activated by the logic device. The output of the slew rate detector is fed to a comparator to be compared with a reference signal, indicative of a predetermined slew rate, supplied by the logic device. When the actual slew rate output exceeds the value of the reference signal, the comparator issues a signal, which after being delayed for a time determined by or programmed into the logic device, activates the energy storage device to issue a second low-energy shock to the heart through the shock delivering electrodes. Additional shocks may be delivered in a manner similar to the delivery of the second shock under the control of the logic device.

In this way, the first shock is delivered with or without regard to synchronization to the arrhythmia being detected. The primary purpose of the first shock, with or without synchronization, is to "coarsen" or alter the configuration of the arrhythmia, primarily by lowering its frequency or by increasing its amplitude. It is theorized, following the work of Kugelberg, that a small portion of the myocardium is organized by the first shock, thus reducing the random electrical activity in the myocardium, and reducing the frequency of the resulting arrhythmic ECG waveform. Further, it is noted through careful analysis of the ECG, that although some arrhythmias, even ventricular fibrillation, appear totally random, there are periodic, predictable, segments of the ECG; this is particularly the case after the waveform is coarsened by a first shock.

The second and subsequent low-level shocks, through the slew rate detector, are synchronized to a particular repeatable characteristic of the arrhythmia being treated. As an example, for ventricular tachycardia, the repeatable characteristic may be the leading edge of the R-wave found within the arrhythmia. For ventricular flutter and certain ventricular tachycardias, where there sometimes are no recognizable R-waves, synchronization may be on polarization waves; for ventricular fibrillation, where there likely are no recognizable R-waves, synchronization may be on the peak of a maximum rise time ECG spike.

Specifically, the detected ECG is analyzed by the slew rate detector and by the logic circuitry. It presently is contemplated that the analysis be by tracking the maximum instantaneous slew rate and by storing the peak slew rate (i.e., the waveform segment exhibiting the fastest rate of change, in this case, rise time or leading edge of the ECG signal). The logic circuitry then effects delivery of a first shock, preferably on the ECG segment showing the highest slew rate, but possibly without regard to synchronization. If shocking in synchrony, the stored peak slew rate is proportioned by pre-programming or by the logic circuitry, and is fed to the "reference" input of a comparator, the other input of which receives actual slew rate signals.

After the first shock, and within a preprogrammed time interval, the device performs by continually updating the signal representing the highest slew rate segment stored in the preceding time cycle. However, if the ECG is showing a steady decrease in slew rate readings (wherein no segment is of a comparable slew rate to that maximum previously stored), the device updates itself by storing a new peak slew rate. Preferably, updating occurs if the new slew rate differs by a predetermined amount from that previously stored. The device similarly updates itself if the slew rate is steadily rising. After appropriate updating, the above-described cycle is repeated until the arrhythmia is broken and the heart returns to normal sinus rhythm.

Certain patients exhibit more manageable arrhythmias, thus obviating the need for the first unsynchronized shock. In this case, as noted above, it is envisaged that the first shock and all subsequent shocks be synchronized to a particular repeatable characteristic of the arrhythmia being treated.

Thus it is a primary object of the present invention to provide a method and apparatus for correcting certain cardiac arrhythmias through the delivery of multiple, properly timed, low-level shocks.

It is a further object of the present invention to provide a method and apparatus wherein the delivery of the low-level shocks is synchronized with a repetitive event occurring in the abnormal cardiac activity.

Still another object of the present invention is to provide a method and apparatus wherein the delivery of low-level defibrillating shocks is synchronized with a portion of the ECG exhibiting maximum slew rate within a predetermined sampling period.

The above and other objects that will hereinafter appear, and the nature of the invention, will be more clearly understood by reference to the following description, the appended claims, and the accompanying drawings.

DETAILED DESCRIPTION OF THE PREFERRED EMBODIMENT

Figure 1:
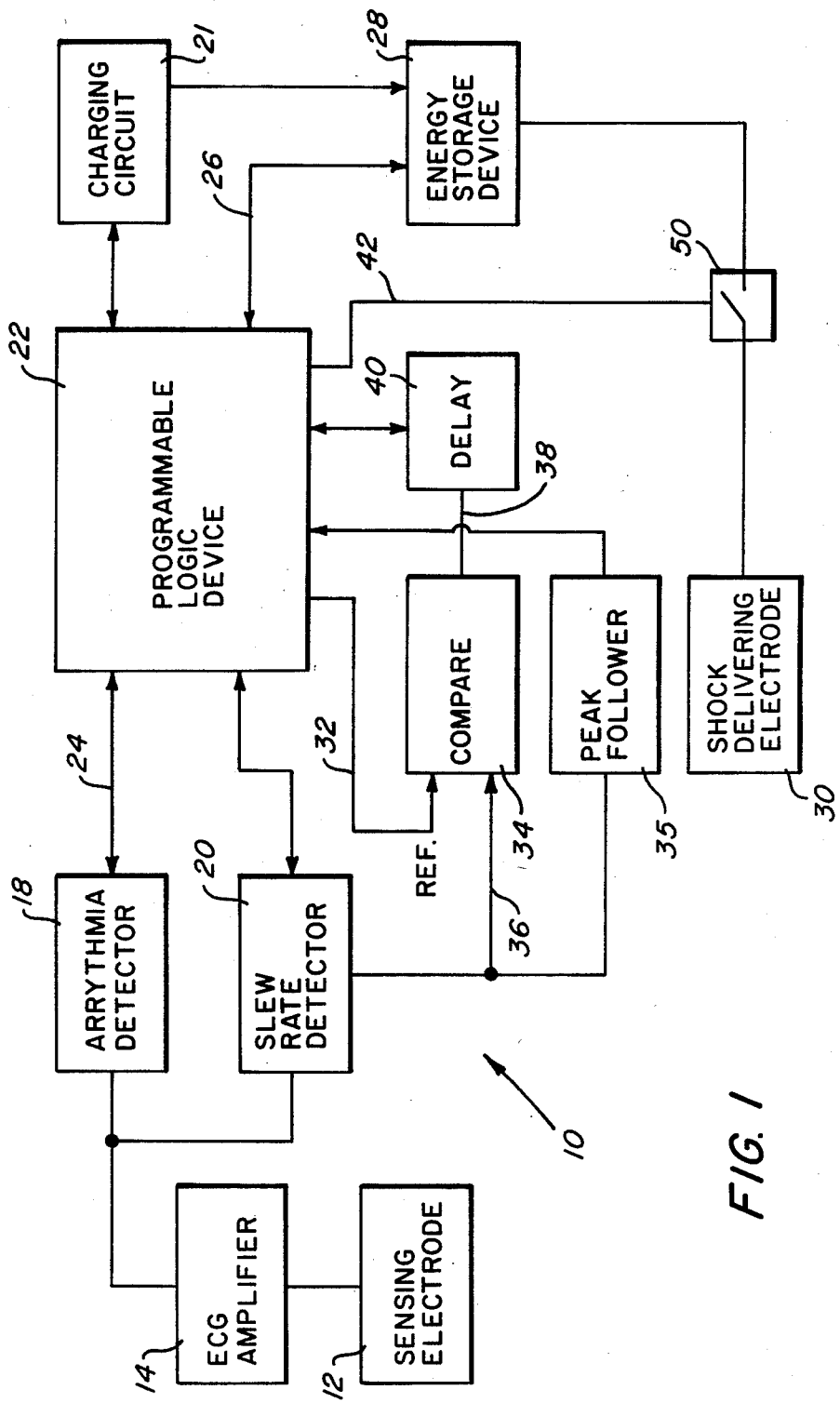
FIG. 1 is a schematic diagram illustrating a preferred embodiment of a device for correcting abnormal cardiac activity adopting the teachings of the present invention.

A preferred embodiment of the device for correcting abnormal cardiac activity in the form of a generally disorganized arrhythmia through the deliverance of multiple low-level shocks is designated at 10 in FIG. 1. The device is implantable in its preferred form. A conventional sensing electrode 12, which acts as a sensing probe, has a pair of electrodes positioned in or about the heart in a position suitable for monitoring the electrical activity (ECG) associated with the heart. For purposes of the present invention, it is essential that the sensing electrode 12 be able to develop precise ECG data so that the electrical logic circuitry can recognize and respond to the repeatable electrical activity that might otherwise go undetected.

An example of one sensing electrode, embodying extracardial base and apex electrodes, is disclosed in Heilman U.S. Pat. No. 4,270,549, incorporated by reference herein. Another example of a known sensing electrode, in the form of an intravascular catheter, can be seen in previously referenced U.S. Pat. No. 3,942,536. It also is contemplated that the sensing electrode 12 take the form of a small, high resolution ECG bipolar sensor having two closely spaced electrodes designed to reside in the right ventricle of the heart.

The electrical activity monitored by the detector 12 is amplified by amplifier 14 and then is fed to an arrhythmia detector 18 and in parallel to a slew rate detector 20 through appropriate leads.

Figure 3:
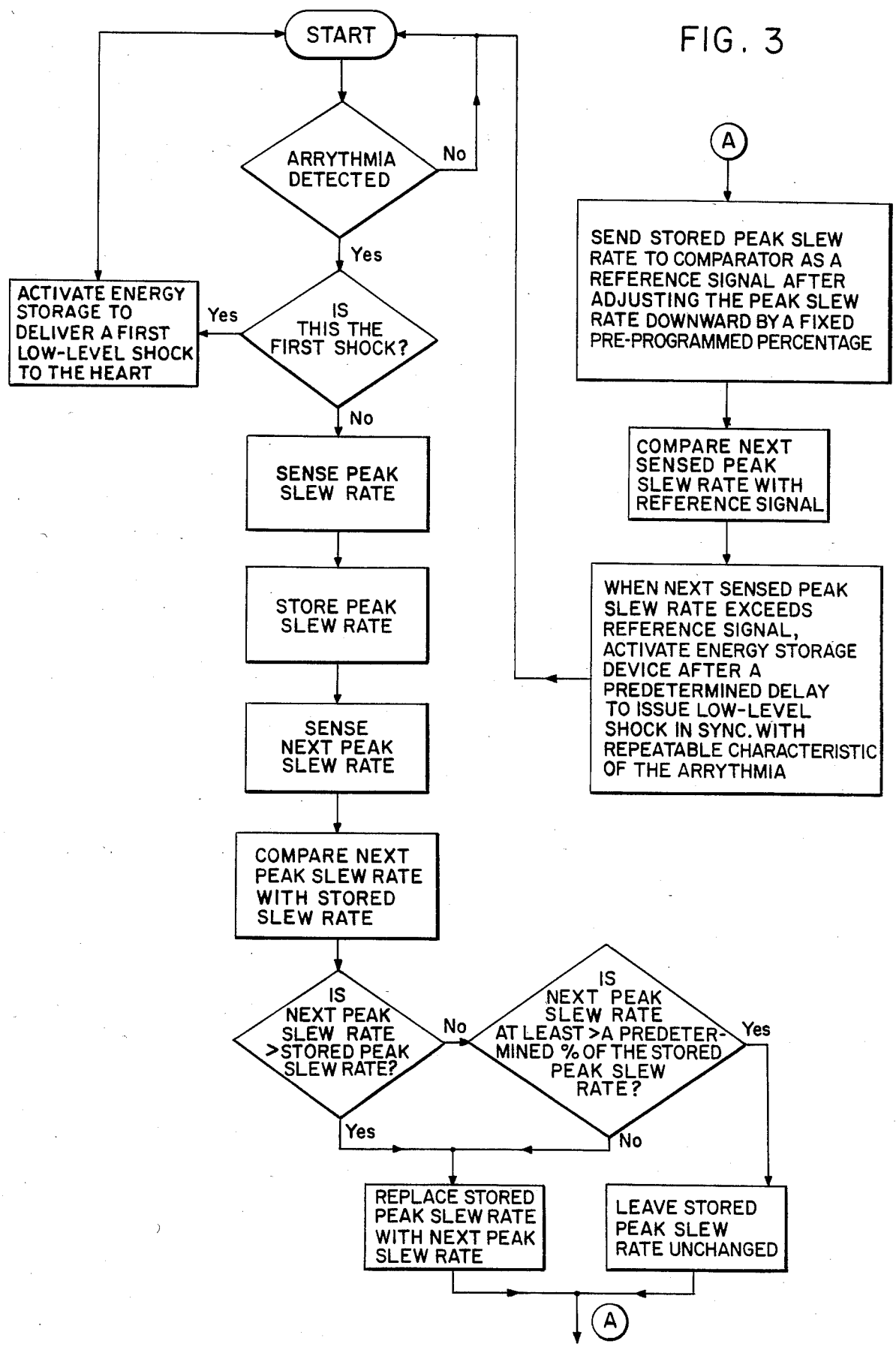
FIG. 3 is a flow diagram to help explain the operation of an embodiment of the device for correcting abnormal cardiac activity.

The arrhythmia detector 18 is designed to detect certain arrhythmias such as ventricular fibrillation, a highly disorganized cardiac rhythm, or ventricular tachycardia, a more organized cardiac rhythm by comparison. One such arrhythmia detector is disclosed in Langer et al U.S. Pat. No. 4,184,493, incorporated by reference herein. Upon detection of one of these arrhythmias, the arrhythmia detector communicates with a programmable logic device 22 via data lines 24. A programmable logic device capable of performing the basic activities to be described, is discussed in copending U.S. patent application Ser. No. 263,910, filed May 15, 1981, incorporated by reference herein and now U.S. Pat. No. 4,393,877. FIG. 3 is a flow diagram showing the basic steps carried out by a preferred embodiment of the device for correcting abnormal cardiac activity in conjunction with the programmable logic device 22. The logic device 22 interprets the data from the arrhythmia detector and issues an appropriate signal on lines 26 in order to activate an energy storage device 28 to deliver a first low-level shock to a shock delivering electrode 30 of known design. Examples of known shock delivering electrodes are the subject matter of previously referenced U.S. Pat. Nos. 4,270,549 and 3,942,536. It also is contemplated that the sensing electrodes and the shock delivering electrodes be combined partially or completely. The energy storage device, which typically is a capacitor, is recharged through a conventional charging circuit 21 under the control of the logic device 22.

The previous description relates to the delivery of the first of a series of shocks. The first shock may be delivered without regard to synchronization, and serves to convert the highly disorganized arrhythmia into a more organized arrhythmia, "coarsening" the arrhythmia. When coarsened, the electrical activity representing the arrhythmia is altered, primarily in terms of its frequency and amplitude, placing it in a more manageable form, so that electrical patterns more easily are recognized. For example, ventricular fibrillation, a highly disorganized arrhythmia, may be coarsened into a ventricular tachycardia or a ventricular flutter, more organized arrhythmias exhibiting more recognizable repeatable characteristics. In like manner, a low amplitude ventricular tachycardia pattern may be changed to a high amplitude pattern, which typically is easier to break.

The logic device issues a predetermined reference signal on lines 32 for input into one port of a comparator 34. The value of the reference signal represents a percentage of the peak slew rate sensed by a peak follower 35 during a preceding timing cycle (which preferably is the slew rate of the ECG segment on which the first shock was issued). For start-up, a predetermined slew rate initially may be incorporated into the system through the programmable nature of the logic device, or an actual slew rate may be detected by the peak follower 35. The reference signal represents a slew rate, on or above which low-level shock therapy is indicated, and continually is updated by the actual slew rate detected by peak follower 35, adjusted by a fixed pre-programmed percent or by other parameters fed into the programmable logic device 22. As an example, the reference signal on line 32 could be 85% of the last peak slew rate detected by peak follower 35.

The slew rate detector 20, under the activation of the logic device 22, now issues an output signal on lines 36 which is fed to the other port of the comparator 34. When the slew rate has a value equal to or greater than that of the reference signal, the comparator issues a signal on line 38 which passes through a delay 40. The period of delay is determined by the logic device, and is set to zero if it is desired to shock on the peak of the ECG segment. After the predetermined delay, a control signal passes on line 42 to activate switch 50 and to pass the energy stored in the energy storage device 28 through the shock delivering electrode 30 to the heart. The deliverance of additional shocks is accomplished in a manner similar to that of the second shock and is carried out until the heart returns to normal sinus rhythm.

The second and subsequent shocks are synchronized to an electrical activity of the heart associated with a repeatable characteristic of the cardiac arrhythmia. As an example, for ventricular tachycardia, the repeatable characteristic may be the leading edge of the R-wave occurring within the arrhythmia (or the zero-crossing of the differentiated ECG signal corresponding to the peak rise time of the R-wave). In this regard, and as described above, it is contemplated that the logic device 22 include timing circuitry to issue discharge commands to the energy storage device 28 so that discharge into the heart through electrode 30 takes place at the desired time relative to the ECG data presented by detector 18 on line 24. Synchronized low-level shocks permit the utilization of lower energy levels to correct certain cardiac arrhythmias. In this way, certain potential dangers associated with high-level shocks, such as tissue damage and the induction of ventricular fibrillation, are minimized.

As noted previously, even ventricular fibrillation, regarded as an arrhythmia whose electrical activity is random, has been found to display certain electrical regularity. Therefore, it sometimes may be possible to issue even the first shock in synchronization with a repeatable characteristic of the ECG. Even when not possible to so synchronize the first shock in VF, second and subsequent shocks typically can be synchronized due to the ECG having been coarsened by the previous shock(s).

Typically, the first and subsequent shocks (for the preferred implantable device) are within the energy range of from about 0.1 joule to about 15 joules. Subsequent shocks typically will be of energies equal to or less than that of the first shock. This is because the more organized arrhythmia (seen after the first shock) should convert to normal sinus rhythm at lower energies than is necessary to convert the previously less organized arrhythmia into the more organized arrhythmia.

Although it is possible that some patients will respond to the first unsynchronized (or synchronized) shock and return to normal sinus rhythm, it is expected that in most cases, multiple low-level shocks will be needed. The major purpose of the first shock is to set up a more organized, manageable arrhythmia exhibiting a repeatable characteristic so that the subsequent synchronized shocks can further organize or eliminate the arrhythmia entirely. In the preferred embodiment, the detectable event on which the synchronized shocks are issued is the peak of the wave most closely resembling an R-wave.

The slew rate detector 20 is employed to synchronize the second and subsequent low-level shocks. If there is a detected slew rate in the timing period that is equal to or higher than the highest rate measured in the previous timing cycle, say, for example, one volt per second, then a shock can be delivered on that particular portion of the waveform, preferably at its peak. Through the programmable logic device 22, the time between pulses can be varied from about 10 milliseconds to about 5 seconds, with a time selection of from about 80 milliseconds to about 1.5 seconds being preferred. It is to be understood that the actual time between pulses is not necessarily continuous. The range is actually broken up into a series of discrete time intervals, typically less than a millisecond in duration. For a preferred embodiment, the discrete time intervals are those within which the peak slew rate is sought. This could occur a short time after the last shock, or could occur two or more timing cycles later if the circuit recognizes the need to update its stored data. In this regard, it is theorized that the effectiveness of any such subsequent shock depends on the energy level, the precision of the synchronization with the particular ECG segment, and the overall elapsed time between it and the first shock.

Figure 2:
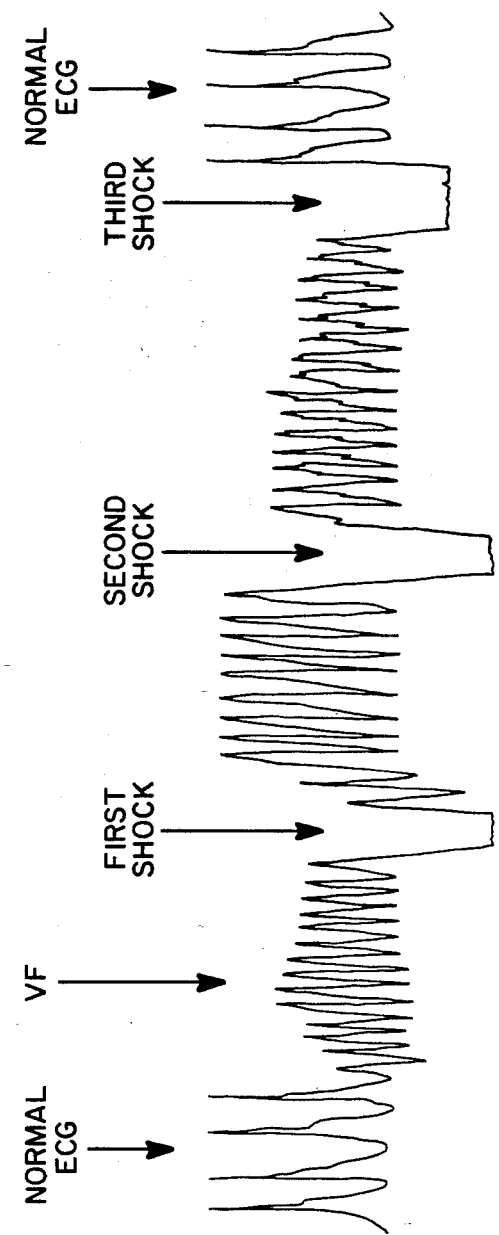
FIG. 2 is a schematic representation of the electrical activity of a heart going from sinus rhythm to ventricular fibrillation, showing the effect of the present invention to return the heart to normal sinus rhythm.

As an example of the device operation, FIG. 2 illustrates an intra-cardiac tracing showing a normal ECG degenerating into ventricular fibrillation, coarsening after a first low-level shock, coarsening further after a second shock, and then returning to normal sinus rhythm shortly after the issuance of a third low-level synchronized shock.

Turning to a related topic, the concept of synchronization of the waveform in ventricular tachycardia already is well accepted. However, synchronization with regard to ventricular fibrillation has never been considered a valid concept because of the rapidity of the waveform and its apparent chaotic nature. Nevertheless, it has been found that with a bipolar sensing electrode having two closely spaced electrodes located in the right ventricle, the ECG waveform, even in ventricular fibrillation, can be specified with sufficient clarity so that observation can be made as to when the wave front passes the bipole, is approaching the bipole, or is receding from the bipole. In addition, the relative distance of the wave front from the bipolar electrode also can be estimated. Thus, with appropriate circuitry as the type described herein, it is possible to synchronize pulses to the fibrillatory waveform and to deliver the pulses in a certain relationship to it. When the relationship of the wave front to the defibrillatory electrodes is favorable, a somewhat greater amount of myocardium can be depolarized, and the waveform coarsened, even if only slightly. Repeated similarly timed shocks would successively capture more and more myocardium until, finally, complete defibrillation is achieved by the succession of shocks, each one ineffective by itself for this purpose. It is likely that the shocks could be delivered either to a small area of the myocardium via a catheter, or globally via epicardial electrodes surrounding the heart. Since the critical timing depends ultimately on the particular geometry and time relationships of the wave front to the sensing electrodes 12, it is not surprising that any fixed interpulse timing, as for example the Kugelberg pulses or the protective zone phenomenon, do not consistently work. On the other hand, the timing relationships of the pulses with respect to the altering innate properties of the wavefront as it is actually depolarizing the heart enables the approach described herein to be effective.

Although it is believed that the approach outlined above can be effective for most arrhythmias, it is desirable to provide a back-up approach should the low-level shocks prove ineffectual. Previous implantable defibrillators deliver larger amounts of energy (in the 35–50 joule range, for example), through the shock delivering electrodes, to eliminate arrhythmic conditions. See U.S. Pat. No. Re. 27,652 for an example of such an implantable automatic defibrillator. It is desirable to incorporate the provision for such higher energy shocks, and in this regard, it is contemplated that the charging circuit 21, under the control of the logic device 22 and solid state switch 50, have the capability of charging the energy storage device 28 with sufficient energy to deliver shocks of up to approximately 30–35 joules.

Although the present invention has been shown and described in terms of a specific preferred embodiment, it will be appreciated by those skilled in the art that changes or modifications are possible which do not depart from the inventive concepts described and taught herein. Such changes and modifications are deemed to fall within the perview of these inventive concepts.

What is claimed is:

1. An apparatus for converting a relatively disorganized arrhythmia to normal sinus rhythm through the intermediary of a more organized arrhythmia having a repeatable characteristic, said apparatus comprising:

sensing electrode means for monitoring the electrical activity of the heart as an ECG signal;

detecting means receiving said ECG signal for detecting the disorganized arrhythmia;

shock delivering electrode means adapted to be secured to the heart;

energy storage means for storing sufficient energy to deliver a low-level shock;

charging means for charging said energy storage means;

discharge means responsive to the presence of the disorganized arrhythmia for causing said energy storage means to deliver a first low-level shock to the heart to bring about the more organized arrhythmia exhibiting a repeatable characteristic;

determining means for determining whether the heart has returned to normal sinus rhythm;

means for activating said charging means when said determining means indicates that the heart has not returned to sinus rhythm and then activating said discharging means for repeatedly delivering further low-level shocks to the heart over a predetermined time period until the heart returns to sinus rhythm; and means for synchronizing the delivery of said further shocks to the repeatable characteristic of the more organized arrhythmia.

2. The apparatus of claim 1, wherein said first and further shocks are of the same magnitude.

3. The apparatus of claim 1, wherein said further shocks are of lower magnitude than said first shock.

4. The apparatus of claim 1, wherein the repeatable characteristic is the leading edge of an R-wave like peak exhibited by the more organized arrhythmia.

5. The apparatus of claim 1, further comprising means for predetermining the time interval between said first shock and the first of said further shocks.

6. The apparatus of claim 1, further comprising means for synchronizing the delivery of said first shock to said repeatable characteristic of said arrhythmia.

7. The apparatus of claim 1 further comprising:
a slew rate detector for receiving said ECG signal from said sensing electrode means;
means responsive to the detection of an arrhythmia by said detecting means for delivering a low-level shock to the heart through said discharge electrode means; and
comparing means for comparing said slew rate with a known reference signal and issuing second and subsequent shocks, during a predetermined time period, to the heart through said shock delivering electrode means, said second and subsequent shocks being issued in synchronism with a repeatable characteristic of the signals sensed by said sensing electrode means.

8. The apparatus of claim 7, wherein said apparatus is implantable.

9. The apparatus of claim 7, further comprising defibrillating means, made active in the event that a predetermined number of low-level shocks are ineffectual, for delivering a defibrillating shock to the heart.

10. The apparatus of claim 7 wherein:
said sensing electrode means includes electrodes adapted to be implanted within the right ventricle of the heart;
said shock delivering electrode means includes a pair of discharge electrode means adapted to be implanted in or about the heart; and
said detecting means includes an arrhythmia detector for receiving signals detected by said sensing electrode means.

11. A method for converting a relatively disorganized arrhythmia to normal sinus rhythm through the intermediary of a nore organized arrhythmia having a repeatable characteristic, said method comprising the steps of:
detecting the presence of the disorganized arrhythmia;
delivering a first low-level shock to the heart to convert the disorganized arrhythmia into a more organized arrhythmia exhibiting a repeatable characteristic;
determining whether the heart has returned to normal sinus rhythm;
repeatedly delivering further low-level shocks to the heart over a predetermined time period until the heart returns to sinus rhythm; and
synchronizing the delivery of said further shocks to the repeatable characteristic of the more organized arrhythmia.

12. The method of claim 11, wherein said synchronizing step comprises synchronizing the delivery of said further shocks to ECG peaks of the more organized arrhythmia.

13. The method of claim 11, and further comprising the step of synchronizing said first shock to a repeatable characteristic of said disorganized arrhythmia.

* * * * *